United States Patent [19]
Weiler et al.

[11] Patent Number: 5,499,457
[45] Date of Patent: Mar. 19, 1996

[54] INFANT LENGTH AND WEIGHT MEASURING APPARATUS

[75] Inventors: Edward B. Weiler, Seattle; Jay A. Jones, Mercer Island; Joseph P. Stefanile, Issaquah; Steven G. Miles, Tacoma, all of Wash.

[73] Assignee: Olympic Medical Group, Seattle, Wash.

[21] Appl. No.: 431,018

[22] Filed: Apr. 28, 1995

Related U.S. Application Data

[63] Continuation of Ser. No. 138,365, Oct. 15, 1993, abandoned.

[51] Int. Cl.⁶ .............................. G01B 7/02; G01G 19/50
[52] U.S. Cl. .................. 33/512; 33/558; 33/833; 177/245
[58] Field of Search .......................... 33/511, 512, 515, 33/503, 556, 558, 561, 783, 784, 803, 804, 805, 807, 832, 833, 3 A; 177/245

[56] References Cited

U.S. PATENT DOCUMENTS

| | | |
|---|---|---|
| 1,555,792 | 9/1925 | Souder . |
| 1,594,255 | 7/1926 | Goldsmith . |
| 1,700,857 | 2/1929 | Schultz . |
| 1,996,553 | 4/1935 | Scully . |
| 2,215,884 | 9/1940 | Runge . |
| 3,020,643 | 2/1962 | Moran . |
| 3,173,208 | 3/1965 | Dana .......................................... 33/3 A |
| 3,438,134 | 4/1969 | Schunk ................................... 33/833 X |
| 3,808,694 | 5/1974 | Hutchinson et al. ...................... 33/512 |
| 4,118,878 | 10/1978 | Semon . |
| 4,143,267 | 3/1979 | Johnson et al. . |
| 4,355,472 | 10/1982 | Wedge . |
| 4,484,394 | 11/1984 | Hsia et al. . |
| 4,495,702 | 1/1985 | Bergstedt . |
| 4,539,754 | 9/1985 | Antony et al. ............................ 33/515 |
| 4,603,828 | 8/1986 | Farley, Jr. et al. . |
| 4,713,888 | 12/1987 | Broselow . |
| 4,765,063 | 8/1988 | Sing . |
| 4,888,877 | 12/1989 | Enderle et al. ........................ 33/503 X |
| 4,896,280 | 1/1990 | Phillips . |
| 4,939,849 | 7/1990 | Johnson . |
| 4,996,994 | 3/1991 | Steinhauer et al. . |
| 5,131,166 | 7/1992 | Weber ................................... 33/558 X |
| 5,174,402 | 12/1992 | Chen .................................... 177/245 X |
| 5,177,875 | 1/1993 | Pienta . |

FOREIGN PATENT DOCUMENTS

| | | |
|---|---|---|
| 602052 | 7/1978 | Switzerland . |
| 2130376 | 5/1984 | United Kingdom . |
| 2215466 | 9/1989 | United Kingdom ..................... 33/783 |
| 9301466 | 1/1993 | WIPO ..................................... 33/561 |

OTHER PUBLICATIONS

Olympic Medical, "The fully automatic scale that takes the work—and guesswork—out of weighing," date unknown.

*Primary Examiner*—Alvin Wirthlin
*Attorney, Agent, or Firm*—Christensen, O'Connor, Johnson & Kindness

[57] ABSTRACT

A device for measuring the length and weight of an infant. The device includes a tray into which the infant is placed. The tray is located on a scale that is used to determine the infant's weight. A length measuring device is located adjacent the tray and includes a wand that extends into the tray and moves slidably along the length of the tray. An infant is placed within the tray so that the head of the infant is adjacent one end of the tray. The wand then slidably moves toward the infant until it contacts the sole of the infant's foot at which time a length measurement is taken. The length measuring device includes a breakaway switch and a rocker switch that stops the movement of the wand if it contacts the infant or another obstruction. The breakaway switch or rocker switch are triggered when the wand is rotated around an axis of rotation approximately perpendicular to the bottom of the tray or the wand is rotated upwardly from the bottom of the tray around an axis of rotation approximately parallel to the bottom of the tray.

9 Claims, 7 Drawing Sheets

INFANT LENGTH AND WEIGHT MEASURING APPARATUS

This is a continuation of the prior application Ser. No. 08/138,365, filed Oct. 15, 1993, now abandoned, the benefit of the filing date of which is hereby claimed under 35 U.S.C. § 120.

FIELD OF THE INVENTION

The present invention relates to devices for measuring the length and weight of an infant and, more specifically, to measuring devices that include safety features to prevent harm to the infant during measurement.

BACKGROUND OF THE INVENTION

Infant length and weight statistics are used to assess and monitor infant growth and health. Thus, accurate methods and apparatus for measuring the length and weight of an infant are necessary for an accurate determination of an infant's health. Length and weight measurements are particularly important for newborn infants where small changes in length and weight affect clinical diagnosis of hypothyroidism, dysmaturity versus intrauterine growth failure and proper nutritional planning.

Infant length and weight measurements are difficult to obtain accurately due to the lack of cooperation by most infants. Newborn infants generally do not fully extend their legs nor do they like it when an individual forces them to extend their legs. In the past, length measurements have frequently been taken using a standard ribbon-type tape measure extended along the length of the infant. Due to the infant's withdrawn legs, it takes one individual to hold the infant and extend at least one leg for measurement and a second individual to actually measure the infant's length.

Some prior art length measuring devices place the infant on a platform such that the crown of an infant's head is placed adjacent a stop at one end of the platform. A slidable guide is then manually moved along the platform toward the infant until it contacts the infant's feet. The distance between the stop on the platform and the slidable guide is then used to determine the infant's length. One such measuring device is described in U.S. Pat. No. 4,939,849, issued to Johnson.

As with other prior art length measuring devices, it is difficult for one person to obtain accurate measurements using the Johnson invention due to an infant's retracted legs. Unfortunately, infants rarely cooperate and stay still with their legs extended in order to allow an operator to manually slide the guide into contact with the infant's feet. Thus, as with other prior art length measuring devices, the Johnson invention requires two people to make accurate measurements, one to hold the infant still and extend at least one leg and the other to move the slidable guide into contact with the infant's feet.

Both infant length and weight measurements are required to properly diagnose infant growth. Thus, it would be beneficial if a single piece of equipment could be used to measure both an infant's weight and length in a single operation. It would also be beneficial if a single nurse or doctor could take accurate infant length and weight measurements without assistance from another person.

A major concern with all infant measuring and weighing devices is avoiding any possible harm to the infant during the measurement process. Infants are easily harmed by being pinched or cut or by falling off of equipment or furniture if they are left unattended for even a minute. Even newborn infants move sufficient amounts to create concern if they are leer unattended on a piece of equipment without proper safety restraints. Thus, precautions must be taken to ensure that an infant is not harmed during length and weight measurements. It is also a concern of doctors and nurses that the equipment used to measure an infant's length and weight be simple to operate, clean up, and maintain.

The present invention is a length and weight measuring device that avoids some of the above-identified disadvantages of the prior art.

SUMMARY OF THE INVENTION

The present invention allows a single operator to easily and accurately measure the weight and length of an infant. An operator may place an infant within the present invention, hold the infant in the proper position and allow the present invention to determine the length and weight of the infant without assistance. Thus, the present invention eliminates some of the disadvantages of prior length and weight measuring devices. In addition, the present invention is easy to operate, easy to clean, and is designed to prevent an infant from being harmed during the measuring process. In the present invention, the infant is placed on a tray that includes four sides or walls that ensure that the infant remains on the platform and does not fall off the platform or get harmed in other ways.

One embodiment of the present invention includes a housing on which a platform is placed. An infant is placed lengthwise on the platform and is located lengthwise along the platform at a predetermined location. An actuated wand coupled to the platform moves slidably along the length of the platform toward the infant until it contacts the infant. The apparatus also includes means for detecting the position of the actuated wand when it contacts the infant and for determining the length of the infant as a function of the position of the wand when it contacts the infant.

In accordance with other aspects of the invention, a scale for measuring the weight of the infant is provided. The platform includes ends and sides adapted to maintain the infant on the platform. The actuated wand is also rotatably coupled to the housing and includes control means to stop the movement of the actuated wand when the wand rotates about an axis of rotation a predetermined amount. In some embodiments, the wand is rotatably coupled to the housing about a first axis of rotation approximately perpendicular to the platform and a second axis of rotation approximately parallel to the platform.

In other embodiments of the invention, means for producing a signal indicative of the location of the wand when it contacts the infant and for determining the length of the infant as a function of the signal are provided. The movement of the wand toward the infant stops when the wand is rotated upon contact with the infant about an axis of rotation either normal to the platform or parallel to the platform. The wand is also movable between a first position in which it extends at least partially across the width of the platform and a retracted position in which it extends along the length of the platform. The wand moves between the extended and retracted positions when it contacts the infant or another obstruction with a predetermined force.

BRIEF DESCRIPTION OF THE DRAWINGS

The foregoing aspects and many of the attendant advantages of this invention will be better appreciated as the invention is better understood by reference to the following detailed description taken in conjunction with the accompanying drawings, wherein.

DETAILED DESCRIPTION OF THE PREFERRED EMBODIMENT

Figure 1:
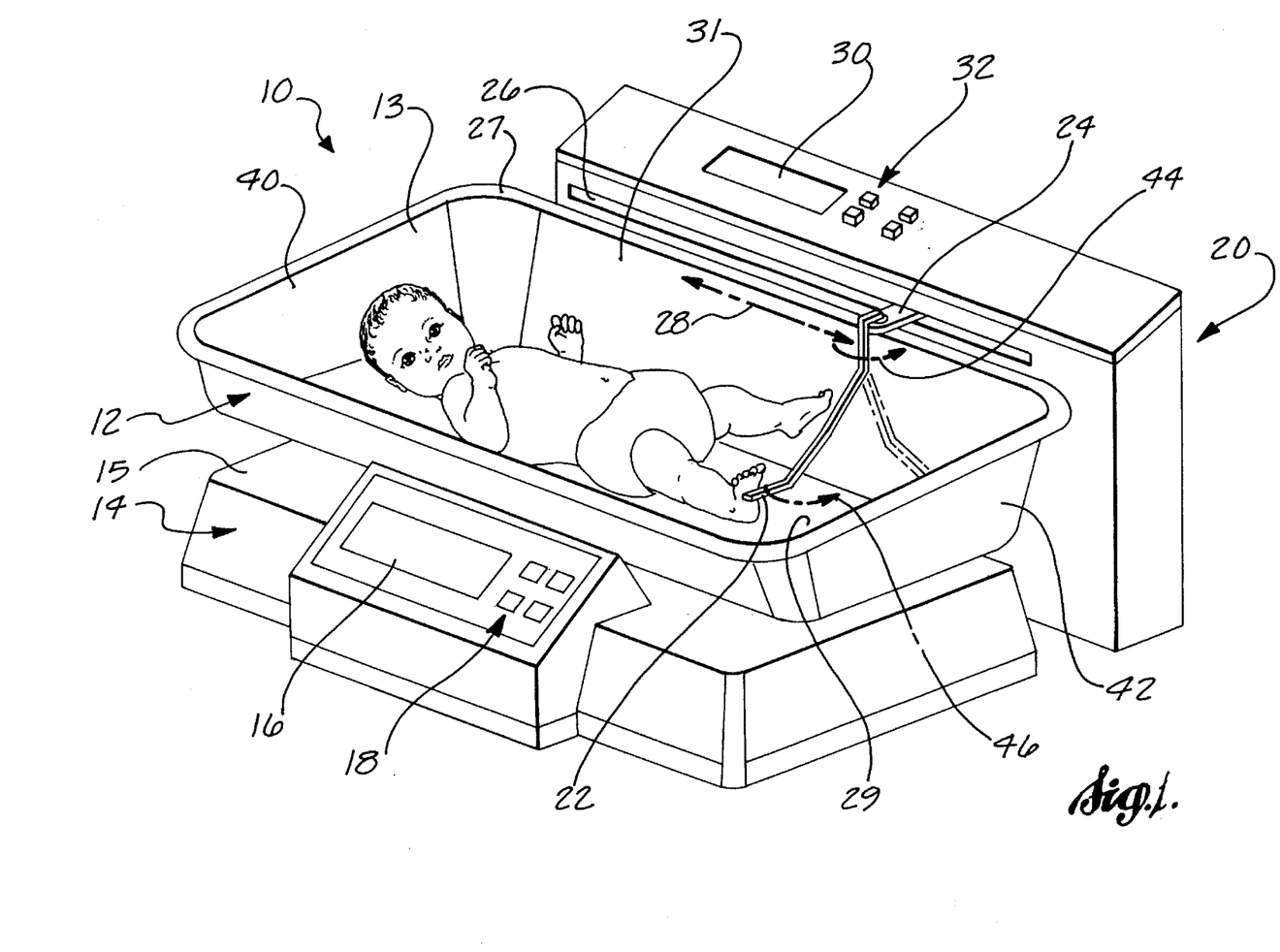
FIG. 1 is a perspective view of a device for measuring an infant's length and weight in accordance with the present invention.

FIG. 1 illustrates a preferred embodiment of a weight and length measuring device 10 according to the present invention. The device includes a platform or tray 12 sized to accept an infant 13. Tray 12 may be formed of any suitable material, such as plastic or metal. In the preferred embodiment, tray 12 includes protective ends and sides that maintain the infant within the tray. Although an infant should never be left unattended in the tray, the tray's protective ends (42, 42) and sides help to maintain the infant within the tray and prevent the infant from moving off of the tray and thus from being harmed. It is advantageous to form the tray from a single piece of a plastic material that can be easily removed and cleaned in case the infant defecates or urinates while the length and weight are being measured. A single piece tray also avoids sharp edges, corners, and holes that could pinch or scratch the infant.

During operation, the tray containing the infant is placed upon the base 15 of a scale 14. The scale 14 may be any suitable scale capable of accurately measuring the weight of an infant. Scale 14 includes a display 16 on which the infant's weight is shown and a control panel 18. In the preferred embodiment, the scale includes an on-off switch, a gram/pound unit selection switch, a zero switch, and a re-weigh switch. In the preferred embodiment, the scale zeroes itself upon being turned on, thus automatically taking into account differing tray sizes and weights. It is also advantageous for the scale to include a zero switch to produce accurate infant weight measurements while accounting for articles added to the tray during weighing, such as blankets or toys.

Prior to weighing, the tray 12 and any other articles to be placed within the tray during weighing, such as a blanket or toy, are placed on the scale and then the zero switch is depressed. The scale 14 then resets the scale weight to zero in order to eliminate the effects of the weight of the tray and added articles on the measured weight of the infant. After zeroing the scale, the infant is placed in the tray and weighed. The resulting value is then output to the user on display 16.

It has been found advantageous for the scale 14 to perform multiple weight measurements of the infant, and to then average the measurements to determine a final infant weight. The use of the average of multiple weight measurements helps to remove measurement errors introduced by any infant movement within the tray during weighing.

In the preferred embodiment shown, a length measuring device 20 is located behind the scale 14 and tray 12. The length measuring device could be an integral part of the scale 14 or it could be an upgrade added to a preexisting scale. Alternately, the length measuring device could be used in combination with a tray without the use of a scale at all.

The length measuring device 20 includes a housing having a wand 22 that is rotatably mounted upon a wand housing 24. The wand housing extends perpendicularly out from the length measuring device and is slidably mounted within a slot 26 in the side of the weight measuring device. The slot 26 extends along the length of the upper portion of the length measuring device slightly above and approximately parallel to an upper lip 27 of the tray. The slot allows the wand and wand housing to be driven to the left or right within the tray by a carriage assembly 70 (FIGS. 3–4), as indicated by arrow 28.

Wand housing 24 and wand 22 extend outwardly approximately perpendicular to the side of the length measuring device and approximately parallel to the bottom 29 of the tray past the lip 27 of the tray. The wand 22 then extends downwardly into the tray approximately parallel to the rear wall 31 of the tray part of the way to the bottom 29 of the tray. The wand then extends perpendicularly at least partially across the width of the tray. This configuration ensures that neither the wand nor wand housing contacts the walls of the tray and that the wand extends sufficiently far into the interior of the tray to be in proper position to contact the infant as the wand moves along the length of the tray. It is important that no part of the wand, wand housing, or length measuring device contact the tray during normal operation of the length and weight measuring device. This ensures that the length measuring device will not interfere with the operation of the scale when the weight measurements are being taken.

During operation, the wand 22 moves to the left, as shown in FIG. 1, toward the feet of an infant placed within the tray until it contacts the sole of the infant's foot. The infant's length is then calculated as a function of the position of the wand when it contacts the infant's foot. The resulting length measurement is then output on a display 30. The length measuring device 20 also includes a control panel 32, having an on/off button, a measure button, a unit of measurement selection button, and a memory button. Greater detail of the actual method of operation of the length measuring device will be discussed below.

Figure 2:
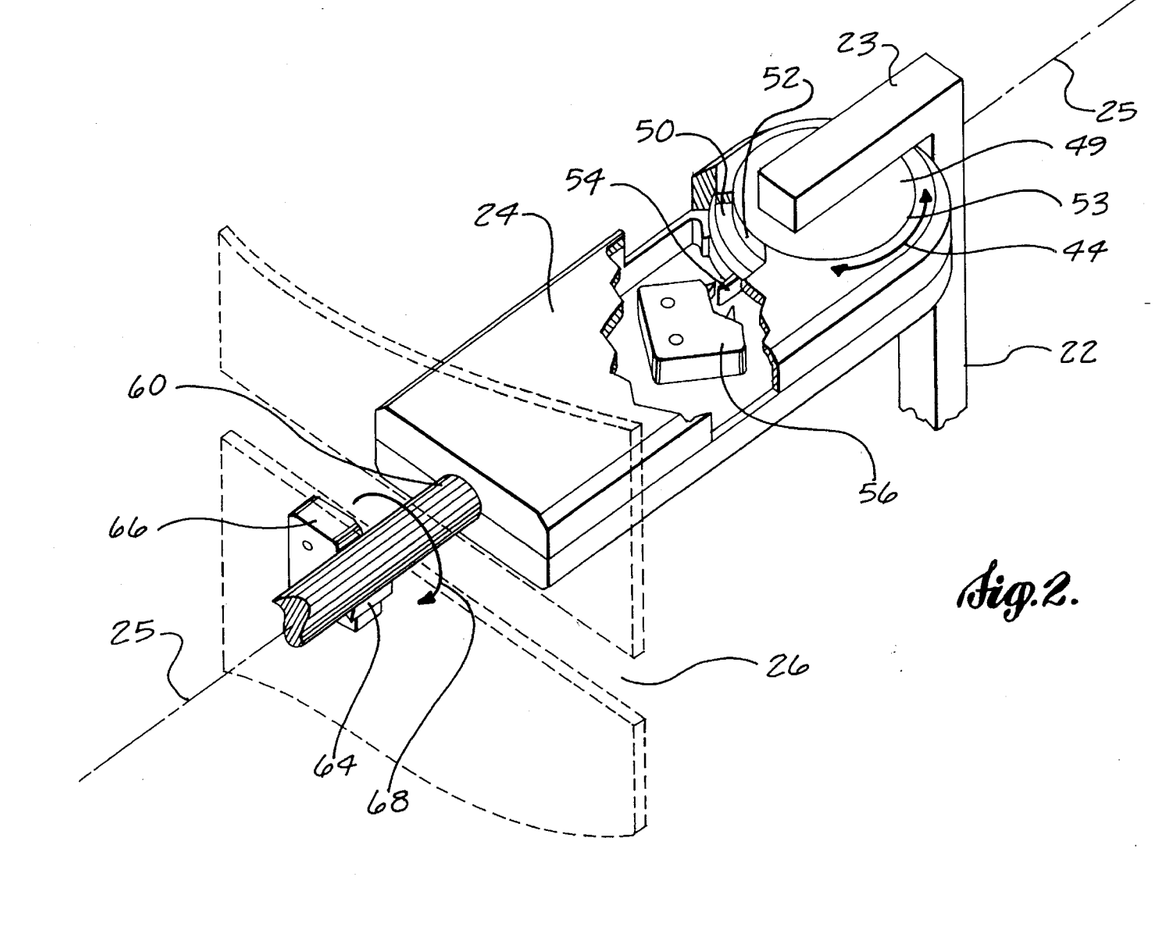
FIG. 2 is an enlarged partial cut-away view of the wand and wand housing of the device of FIG. 1.

The internal mechanics of the preferred embodiment of the length measuring device 20 will now be described by reference to FIGS. 2–4. As best seen in FIG. 2, the top portion 23 of the wand is rotatably attached to the wand housing 24 that extends out from the slot 26. Specifically, the top portion 23 of the wand is attached to the upper surface 49 of a torsion spring 50 that is rotatably mounted within housing 24.

Torsion spring 50 includes a cylindrical bearing 52 on the top of the torsion spring. The cylindrical bearing 52 cooperates with a cylindrical opening 53 in the top of the wand housing to allow the torsion spring 50 and attached wand to rotate clockwise or counterclockwise, as indicated by arrow 44 (FIG. 1). Torsion spring 50 biases the wand toward an operating position in which the wand extends perpendicularly across the width of the tray along the center line 25 of the wand housing (FIG. 2). The torsion spring 50 may be any suitable biasing mechanism capable of supplying a sufficient biasing force to maintain the wand in its centered position during normal operation of the length measuring device. In alternate embodiments, torsion spring 50 could be replaced by other biasing means, including linear springs. An arm 54 extends perpendicularly out from the side of the torsion spring to engage an electrical breakaway switch 56 when the wand rotates clockwise or counterclockwise.

As the wand rotates, it rotates the torsion spring 50 and arm 54 in the same direction. The wand's, and thus arm's, rotation triggers the breakaway switch 56 which opens a circuit, as described in more detail below, and causes the wand's movement to stop or returns the wand to a "home" position at the right of the tray (FIG. 1).

If the wand 22 contacts the infant or another obstruction and the breakaway switch malfunctions, the wand may continue to move toward the infant or obstruction. In this case, the wand may be rotatably displaced clockwise or counterclockwise against the biasing force of the torsion spring 50, as shown by arrow 44. This rotational movement of the wand allows it to move to a retracted position, as shown in phantom in FIG. 1. When the wand is in the retracted position, the wand housing and wand may continue to move along the length of the tray without extending outwardly into the tray and without possibly harming an infant located in the tray.

The biasing force of the torsion spring 50 is selected to be of a magnitude to bias the wand toward the central position illustrated in FIG. 2, but is insufficient to prevent the wand from rotating clockwise or counterclockwise, as indicated by arrow 44, upon contact with the infant or other obstruction. Thus, the biasing force of the torsion spring is selected to be of a magnitude to allow the wand to rotate before the force exerted by the wand results in harm to either the infant or the length measuring device.

The end of the wand housing 24 opposite the wand is attached to a shaft 60. Shaft 60 extends through the slot 26 in the length measuring device (FIG. 1) and is rotatably mounted in a support arm 62 (FIG. 3). The support arm 62 is attached to a carriage assembly 70 that moves the wand housing and wand along the length of the tray as described below.

Shaft 60 includes a rocker arm 64 (FIG. 2) that extends perpendicularly out from the surface of the shaft over part of the length of the shaft. Rocker arm 64 is located on shaft 60 such that it contacts and triggers a rocker switch 66 mounted on the side of the support 62 when the wand and wand housing are rotated clockwise as shown by arrow 68 in FIG. 2, i.e., when the wand is displaced rearwardly by contact with the infant, as shown by arrow 46 in FIG. 1. Movement of the rocker arm triggers the rocker switch 66, which causes the movement of the wand to stop, and a length measurement to be determined, as described below. The combination of the rotatably mounted shaft 60, rocker arm 64, and rocker switch 66 allows the point of contact between the wand and infant's feet to be determined. The rocker switch also helps to ensure that the movement of the wand stops upon contact with the infant, thus preventing the infant from being harmed.

It may be advantageous to include a biasing means, such as a spring (not shown), on the shaft 60. The biasing means would bias the wand housing and wand counterclockwise as shown in FIG. 2 so that the wand is maintained perpendicular to the plane of the tray until it contacts the sole of the infant's foot. The biasing means would help to ensure accurate length measurements by helping to eliminate accidental triggering of a length measurement upon touching the wand.

The magnitude of the centering force provided by the torsion spring 50 and biasing means on shaft 60 allows the wand to be displaced rearwardly, as shown by arrow 46, upon contact with an infant's foot or other obstruction prior to the wand rotating clockwise or counterclockwise as shown by arrow 44. Thus, upon contact with an infant's foot the wand will first be displaced rearwardly triggering the rocker switch 66 which triggers a length measurement and stops the wand's movement. Only upon contact with an unintended obstruction or upon improper operation of the length measuring device will the wand be rotatably displaced, as shown by arrow 44. Both the rocker switch and breakaway switch act as safety measures to ensure that movement of the wand stops upon contact with the infant or other obstruction.

Figure 3:
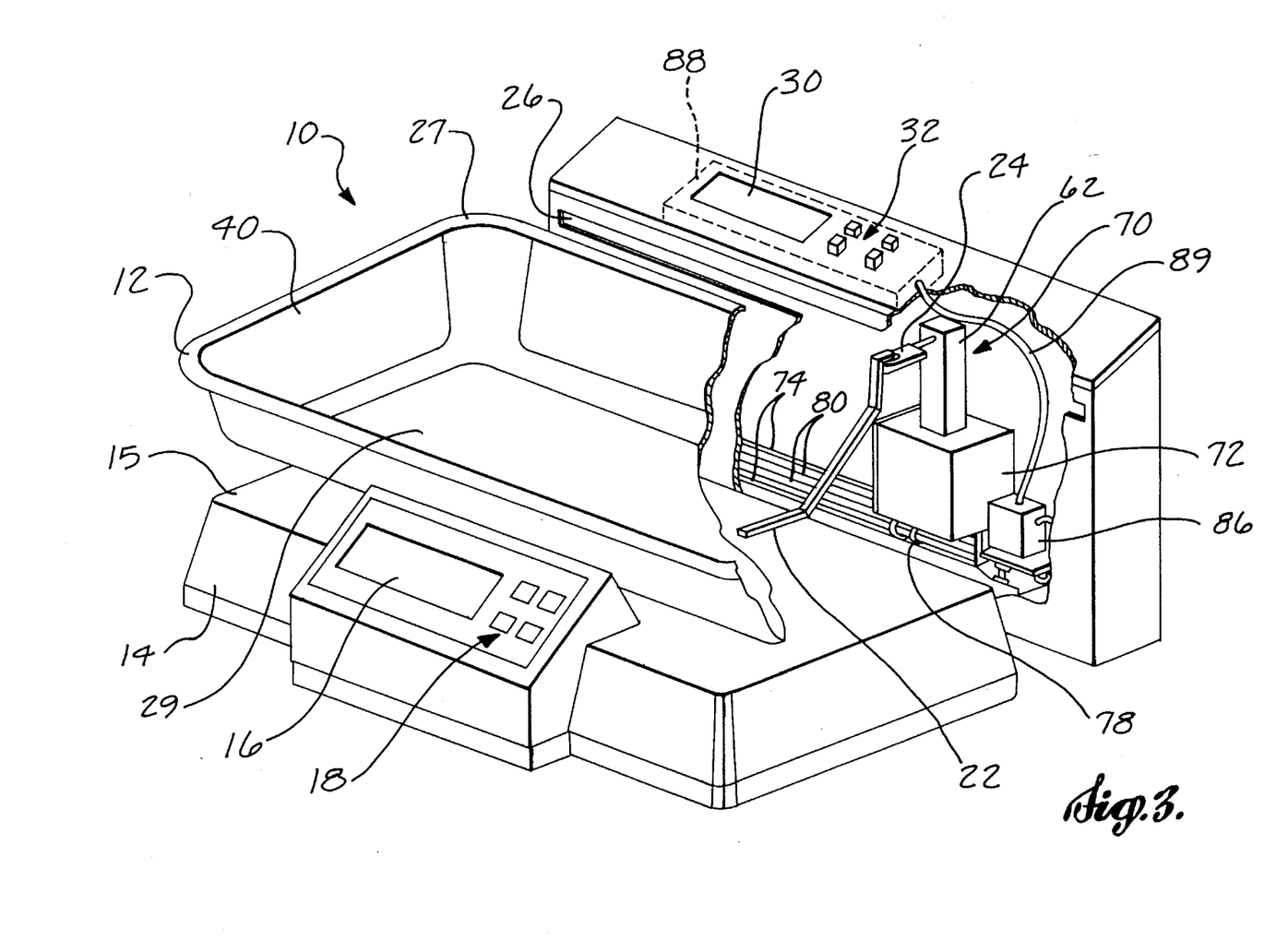
FIG. 3 is a partial cut-away view of the carriage assembly of the infant measuring device of FIG. 1.
Figure 4:
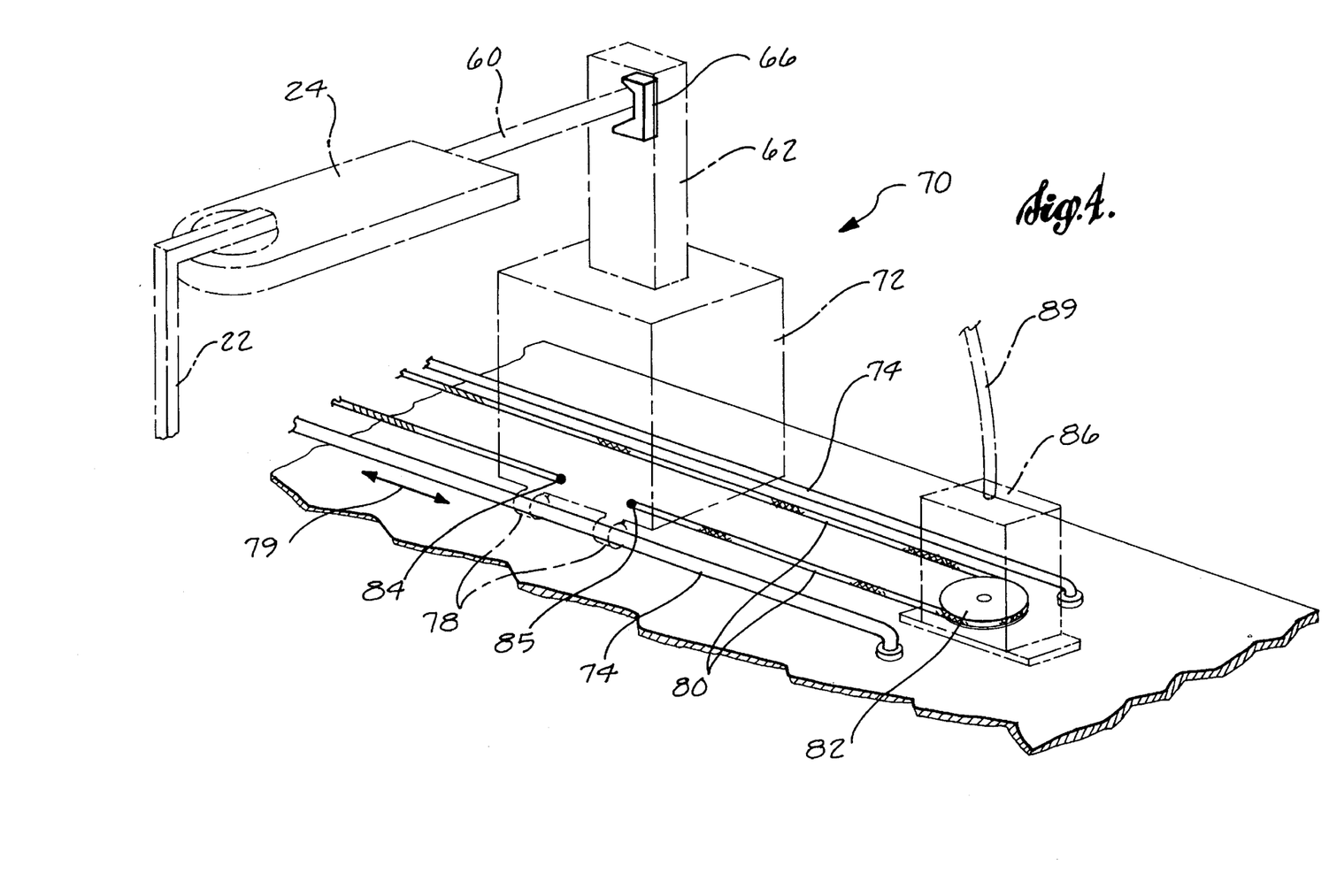
FIG. 4 is an enlarged partial cut-away view of the carriage assembly of FIG. 3.

As best illustrated in FIGS. 3 and 4, the wand 22, wand housing 24, and rocker switch 66 are all mounted on support 62. The support 62 is mounted upon a carriage assembly 70 that moves the wand over the length of the tray in a manner similar to drive carriages used in dot matrix printers. The carriage assembly 70 includes two parallel carriage rods 74 that extend along the length of the length measuring device. A carriage housing 72 is slidably mounted on the carriage rods 74 through the use of two cylindrical guides 78 located on opposing sides of the bottom of the carriage housing. Guides 78 encircle the carriage rods 74 and allow the carriage housing to slide to the left and right as indicated by arrow 79.

One end of a drive cable 80 is attached to the left side of the carriage housing at an anchor point 84. The drive cable extends from anchor point 84 to the left end of the length measuring device and then passes around a rotatably mounted pulley (not shown). The drive cable then extends back to the right end of the length measuring device and passes around a drive pulley 82. Finally, the opposite end of the drive cable is attached to the carriage housing at an anchor point 85 located on the right side of the housing. Rotational movement of the drive pulley 82 moves the cable 80 clockwise or counterclockwise in order to move the carriage housing, and thus wand, to the left or right, respectively.

Drive pulley 82 is connected to a drive mechanism 86 that is in turn connected to a central processing unit "CPU" 88 by a conductor 89. In the preferred embodiment, the drive mechanism includes circuitry to inform the CPU of the location of the carriage housing and the wand as it moves either left or right. Rocker switch 66 and breakaway switch 56 are also connected to the CPU.

During operation, the wand and wand housing begin in a home position to the extreme right of the tray 12 as shown in FIG. 1. An infant is then placed within the tray such that the crown of the infant's head is adjacent the left wall 40 of the tray and the body and legs of the infant extend along the length of the tray. The operator then holds the infant so that at least one leg is fully extended along the length of the tray and the foot is slightly pronated so that the sole of the foot is perpendicular to the bottom of the tray. The operator then pushes the length measurement button on the control panel 32. The carriage assembly then moves the wand to the left toward the infant until the wand contacts the sole of the infant's foot at which time the wand is displaced rearwardly as shown by arrow 46 (FIG. 1).

Displacement of the wand triggers the rocker switch 66 and causes the CPU to record the position of the wand when it contacts the sole of the infant's feet. Knowing the position of the wall 40, the CPU uses the position of the wand when it contacts the infant's foot to determine the length of the infant. After contact with the infant's foot, the wand moves to the right away from the infant. In the preferred embodiment, it has been found advantageous to have the wand move to the right away from the infant approximately 2.5 inches and then to take a second and third measurement of the infant's length. The CPU can then display all three length measurements or average the three length measurements. In the preferred embodiment, it has been found most advantageous to display all three length measurements. This allows the operator to observe any discrepancies in the three length measurements, thus giving an indication of whether or not more measurements should be taken. If the three length measurements differ substantially, an error occurred during the measurement process and the length of the infant should be remeasured. After the infant's length is determined, it is output on display 30 and the wand returns to its home position.

As described above, when the wand contacts the infant or other obstruction, the rocker switch 66 is triggered, stopping the wand's movement. If the rocker switch should malfunction, continued movement of the wand toward the obstruction causes the wand to rotate away from the obstruction (FIG. 1), triggering the breakaway switch 56 and stopping movement of the wand. Even if both the rocker switch and breakaway switch malfunction, the wand continues to rotate out of the way of the obstruction to a retracted position shown in phantom in FIG. 1. The retracted position allows the wand to continue moving along the length of the tray without presenting any possible harm to the infant.

In addition to the safety features described above, the motor 86 is also sized so that it will stall when the wand housing or wand contacts the infant or another obstruction with a predetermined force. Sizing the motor ensures that the wand and wand housing are not driven with sufficient force to harm the infant.

Figure 7:
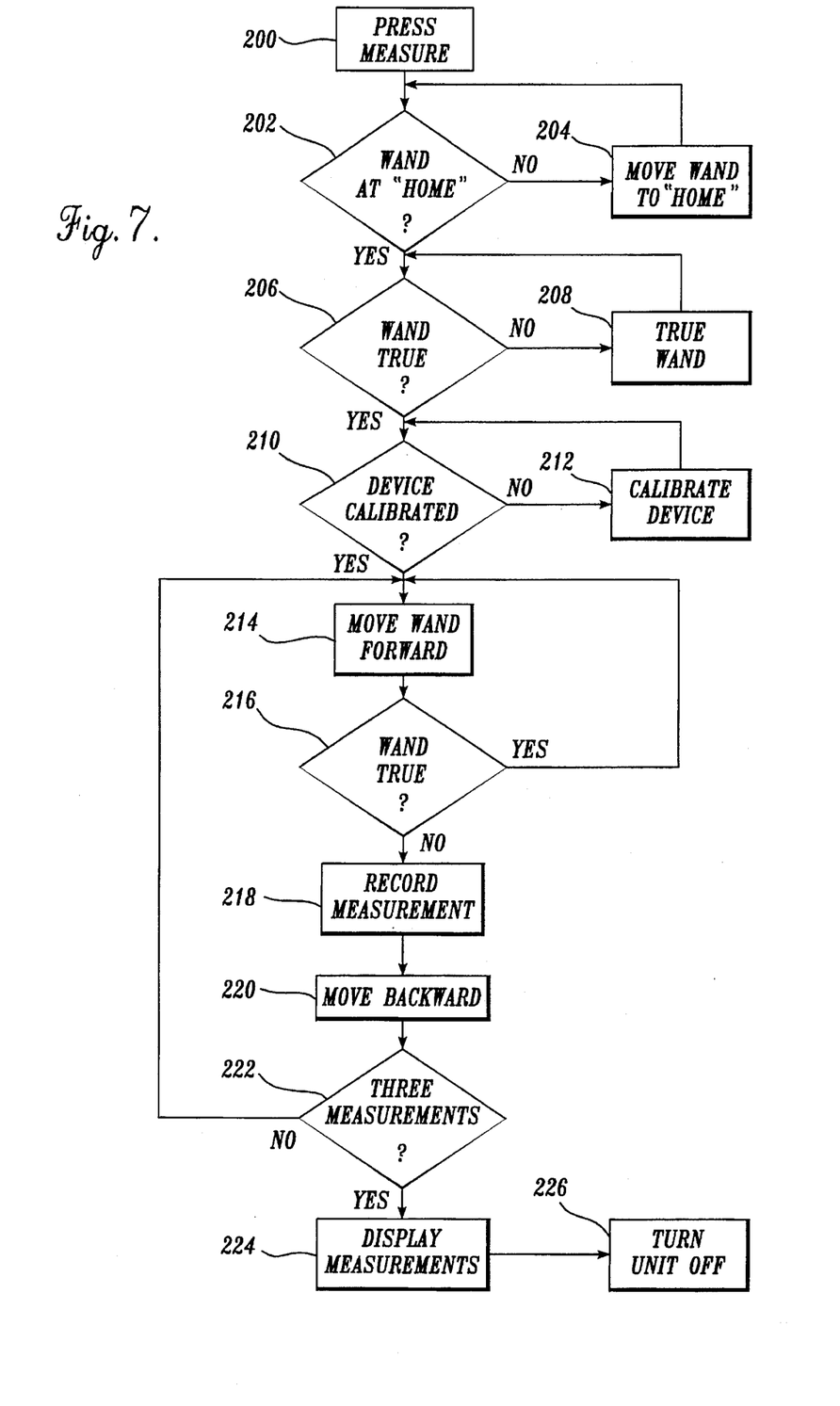
FIG. 7 is a flow chart of a method of operation of the preferred embodiment of the infant length and weight measuring device of FIG. 1.

The logical operation of a preferred embodiment of the present invention will now be described with reference to the flow chart illustrated in FIG. 7. After the infant has been placed within the tray, the operator presses the measure button on the control panel 32 as shown in block 200. The CPU then determines whether or not the wand is at its home position as shown in block 202. If the wand is not at its home position, it is moved to its home position as shown in block 204. Otherwise, the CPU determines whether or not the wand is "true," i.e., whether or not the wand is extended perpendicularly across the width of the tray. If the wand is not true, the CPU informs the operator to true the wand as shown by block 208.

If the wand is true, the CPU determines whether or not the device has been calibrated as shown in block 210. If the system has not been calibrated, the CPU informs the operator to perform the calibration measurement as shown in block 212. The device is calibrated by placing a calibration rod within the tray so that the rod is in contact with the wall 40 at one end and extends perpendicular to the wall 40 along the length of the tray. The operator then informs the CPU to perform a calibration algorithm that causes the wand to move across the tray until it contacts the calibration rod. The CPU then resets its internal calibration to correspond to the known length of the calibration rod.

If the system has already been calibrated, the wand moves forward toward the infant's foot as shown in block 214. The CPU then monitors the rocker switch 66 and breakaway switch 56 to determine whether or not the wand is true, i.e., has not contacted the infant or an obstruction, as shown in block 216. As long as neither the rocker switch nor breakaway switch have been triggered, the wand continues its movement toward the infant. If either the breakaway switch or rocker switch are triggered, the CPU stops the movement of the wand and records a length measurement as shown in block 218.

After recording the length measurement, the wand moves backwards 2.5 inches as shown in block 220. The CPU then determines whether three length measurements have been taken as shown in block 222. If less than three length measurements have been taken, the CPU performs the steps of blocks 214–220 until three length measurements are completed. After three length measurements have been completed, the CPU displays the results to the operator as shown in block 224. The CPU then turns the unit off as shown in block 226.

Figure 5:
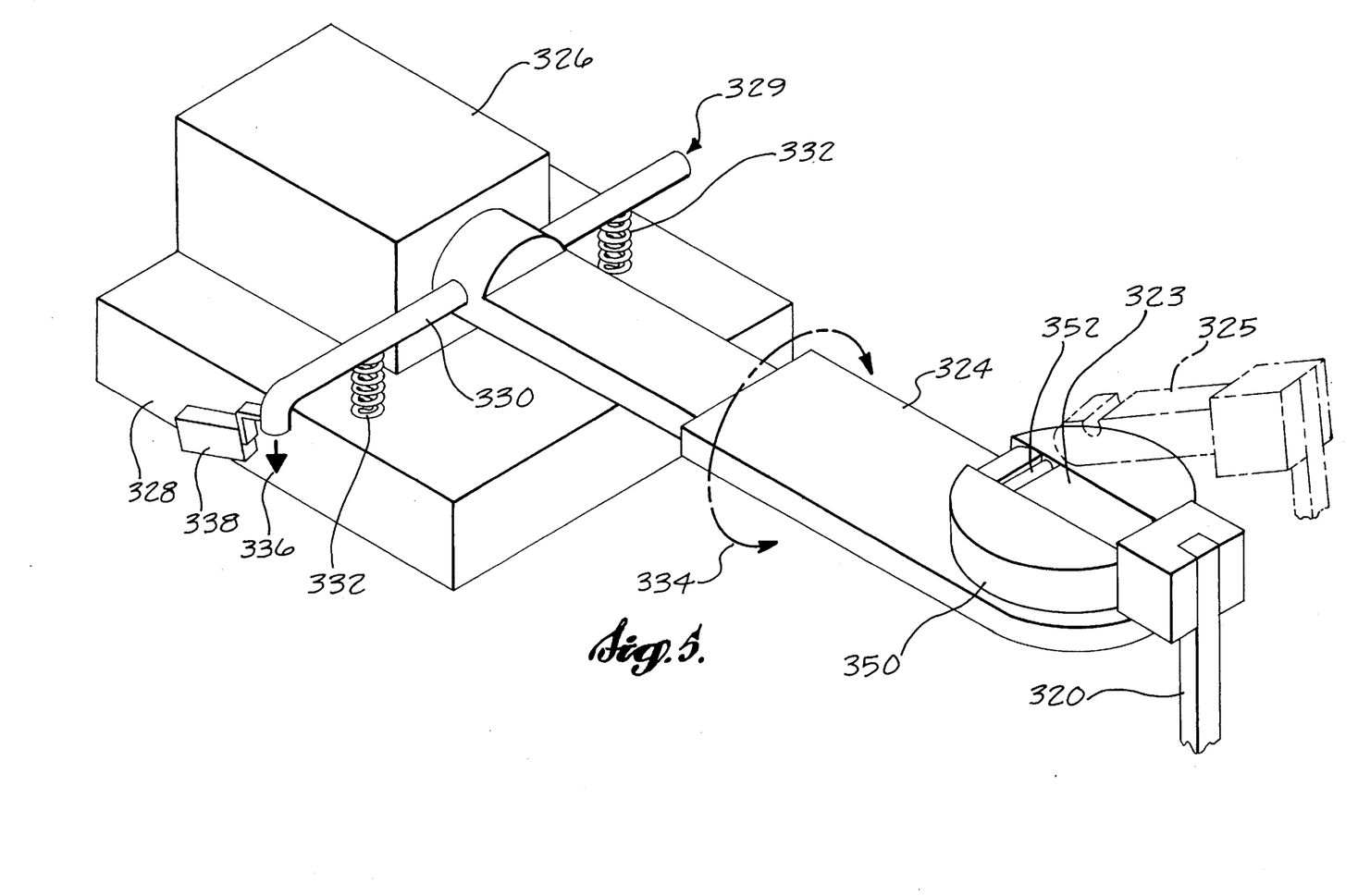
FIG. 5 is a view of a second embodiment of the wand and wand housing.

A second embodiment of the wand and wand housing is illustrated in FIG. 5. Features of the second embodiment not described herein are similar to the features described with respect to the first embodiment and may be understood by reference to the description of the first embodiment. In the second embodiment, the wand housing 324 includes a torsion spring 350 located at one end. The torsion spring 350 is rotatably connected to the wand housing through the use of a suitable fastening device such as a screw-type fastener (not shown). The upper surface of the torsion spring includes a slot extending across its width into which the wand 320 is removably inserted. A rod 352 extends across the slot at one end of the torsion spring.

The wand 320 includes an arm 323 at its uppermost end. The arm 323 includes a slot 325 sized to engage and accept the rod 352. The combination of the arm 323, slot 325, and rod 352 allows the wand to be releasably coupled to the torsion spring and thus wand housing. As shown in phantom in FIG. 5, the wand is placed within the slot in the torsion spring such that the slot 325 in the arm is placed underneath and engages rod 352. The wand is then lowered into place within the slot.

The wand housing 324 is rotatably attached to a support arm 326 at the end opposite the torsion spring. The support arm 326 is in turn attached to the carriage housing 328. The end of the wand housing opposite the torsion spring also includes a biasing means 329 that biases the wand housing and wand into a central position such that the wand remains approximately perpendicular to the platform. The biasing means 329 includes a rod 330 that extends through the wand housing 324. Springs 332 extend between the rod 330 and housing 328 on both sides of the rod. The springs 332 bias the rod and thus wand housing into its central position.

As the wand 320 is displaced rearwardly upon contact with an infant, the wand and wand housing rotate counterclockwise as shown by arrow 334. This rotational movement of the wand housing causes one end of the rod 330 to move downwardly as shown by arrow 336 to contact a rocker switch 338. Triggering the rocker switch 338 stops the movement of the carriage assembly and informs the CPU to take a length measurement in a manner similar to that described with respect to the first embodiment.

The second embodiment does not include a break-away switch coupled to the torsion spring. In the second embodiment, the length measuring device is simplified by eliminating the break-away switch and depending upon the rocker switch 338, break-away, and stalling of the motor driving the carriage assembly to ensure that the movement of the wand does not harm the infant.

Figure 6:
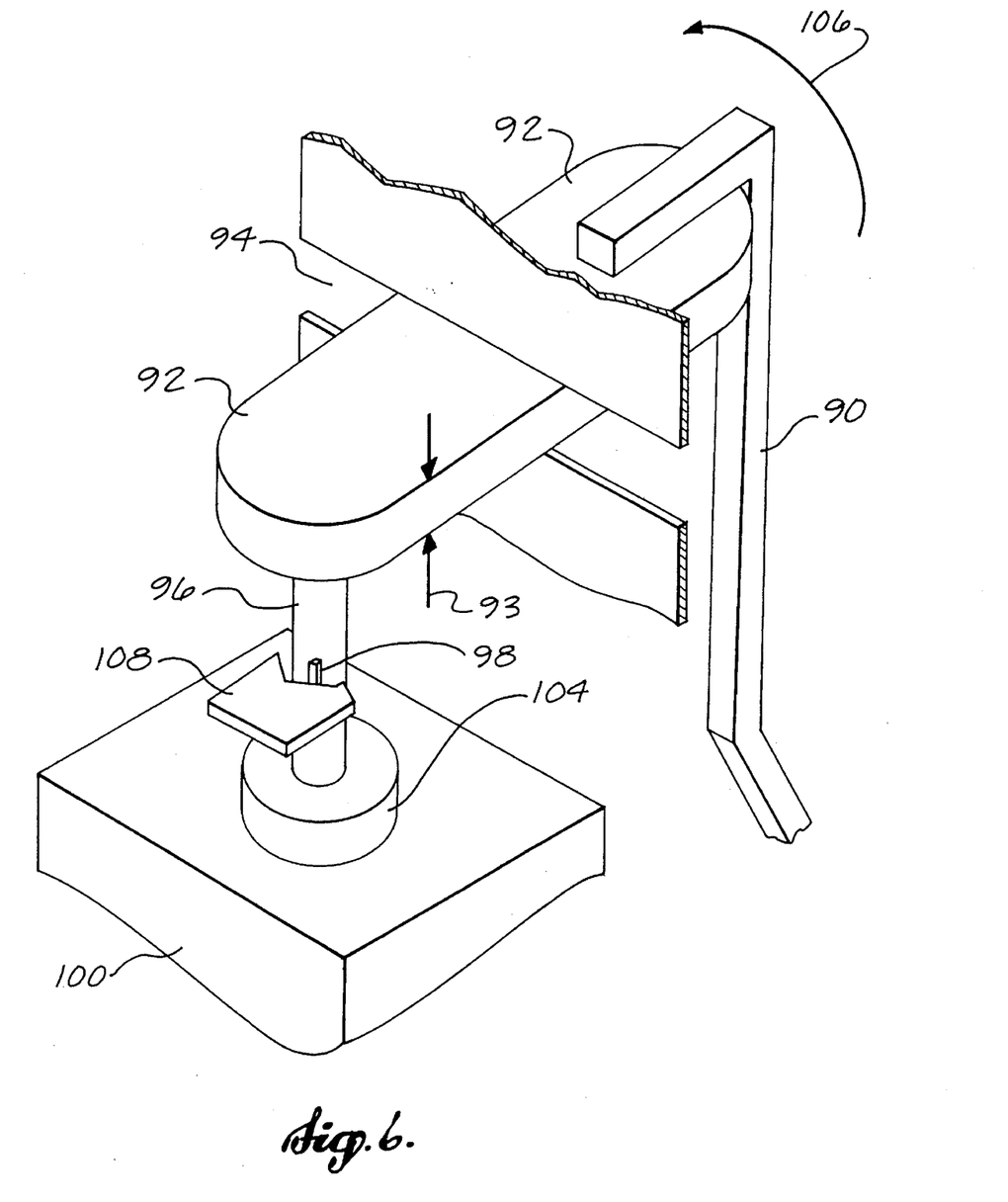
FIG. 6 is an enlarged partial cut-away view of an alternate embodiment of the wand and wand housing.

An alternate embodiment of the wand and wand housing is illustrated in FIG. 6. Aspects of the alternate embodiment not described below may be understood by reference to the detailed description of the first embodiment. One goal of the alternate embodiment is to simplify the mechanics of the wand housing. In the alternate embodiment, the wand 90 is fixedly attached to a flat plate wand housing 92 having a thickness 93. Wand housing 92 extends through the slot 94 and is rigidly attached to a shaft 96 at the end of the wand housing opposite the wand. Shaft 96 is rotatably mounted on a carriage housing 100.

A torsion spring 104 is mounted on the carriage housing 100 and coupled to the shaft 96 such that the torsion spring biases the wand into a centered position in which the wand extends partially across the width of the tray (not shown). The magnitude of the force supplied by the torsion spring 104 maintains the wand in position during normal operation and allows the wand and wand housing to be rotationally displaced as shown by arrow 106 if the wand contacts an unintended obstruction with sufficient force.

A rocker arm 98 extends outwardly from the surface of the shaft 96 partially along its length. The rocker arm 98 triggers a rocker switch 108 when the wand and wand housing are rotationally displaced. Triggering the rocker switch 108 causes the wand's movement to stop and the CPU to take a length measurement in a manner similar to that described with respect to the first embodiment. The alternate embodiment allows the complexity of the wand housing and wand assembly to be reduced but decreases the freedom of movement of the wand.

In still other embodiments, the wand could include a touch sensitive switch in addition to or instead of the rocker switch and breakaway switch. The touch sensitive switch could be placed on the surface of the wand such that it is triggered by contact with the infant. In this embodiment, the wand could also rotate to increase safety or could be fixedly attached to the wand housing.

While the preferred embodiment of the invention has been illustrated and described, it will be appreciated that various changes can be made therein without departing from the spirit and scope of the invention.

The embodiments of the invention in which an exclusive property or priviledge is claimed are defined as follows:

1. An apparatus for measuring the length of an infant, the apparatus comprising:

a housing;

a platform on which the infant is placed lengthwise removably coupled to the housing, the platform including a wall at one end, the wall locating the infant lengthwise on the platform when one end of the infant is placed adjacent the wall;

an actuated wand that extends at least partially across the width of the platform and that moves toward the infant when the infant is placed on the platform and that stops when the wand contacts the infant;

a drive mechanism that actuates the wand, the wand being rotatably coupled to the drive mechanism about an axis approximately normal to the platform, the drive mechanism stopping the movement of the wand toward the infant when the wand rotates about the axis of rotation;

means for detecting a position of the actuated wand when the wand contacts the infant; and means for determining the length of the infant as a function of the position of the actuated wand when the wand contacts the infant.

2. The apparatus of claim 1, further comprising a scale for measuring the weight of the infant, and wherein the platform is located upon the scale.

3. The apparatus of claim 1, wherein the platform includes ends and sides adapted to maintain the infant on the platform.

4. The apparatus of claim 1, wherein the actuated wand is rotatably coupled to the drive mechanism about a second axis of rotation approximately parallel to the platform.

5. An apparatus for measuring the length and weight of an infant, the apparatus comprising;

a scale having a base;

a platform removably placed on the base, the platform including an upwardly extending wall that locates the infant when the infant is placed lengthwise on the platform with one end of the infant located adjacent the wall;

a measuring device coupled to the scale, the measuring device including:

a measuring wand that extends at least partially across the width of the platform;

a drive mechanism that moves the wand lengthwise toward and away from the infant;

means for detecting the position of the wand when it contacts the infant;

means for determining the length of the infant as a function of the position of the wand when the wand contacts the infant, the wand being rotatably coupled to the drive mechanism about an axis extending approximately normal to the platform; and a switch coupled to the wand, the switch stopping the movement of the wand when the wand rotates about the axis of rotation upon contact with the infant.

6. The apparatus of claim 5, wherein the wand rotates about a second axis extending approximately parallel to the platform and wherein the switch stops the movement of the wand toward the infant when the wand rotates about the axis approximately parallel to the platform upon contact with the infant.

7. The apparatus of claim 5, wherein the wand rotates about the axis approximately normal to the platform to a retracted position in which the wand extends approximately parallel to the length of the platform upon contacting the infant with a predetermined force.

8. An apparatus for measuring the length and weight of an infant, the apparatus comprising:

a scale having a base onto which a load to be measured is placed;

a platform removably coupled to the base, the platform including upwardly extending walls that form a cavity that prevents an infant placed on the platform from moving off of the platform, one of the walls locating the infant lengthwise on the platform when one end of the infant is located adjacent the wall;

a measuring device coupled to the scale, the measuring device including:

a wand that extends at least partially across the width of the platform and downward into the interior of the cavity;

a drive mechanism that moves the wand lengthwise toward and away from the infant, the wand being rotatably coupled to the drive mechanism about an axis approximately normal to the platform;

means for detecting the position of the wand when it contacts the infant;

means for determining the length of the infant as a function of the position of the wand when it contacts the infant;

means for stopping the movement of the wand lengthwise towards the infant when the wand rotates about the axis upon contacting the infant; and means for allowing the continuing rotation of the wand about the axis approximately normal to the platform to a retracted position in which the wand extends lengthwise to the platform and lies adjacent to one of the walls extending upwardly from the platform.

9. The apparatus of claim 8 wherein the wand rotates about a second axis extending approximately parallel to the platform and wherein the apparatus further comprises a second means for stopping the movement of the wand toward the infant when the wand rotates about the axis approximately parallel to the platform.

* * * * *